(12) United States Patent
Marple-Horvat

(10) Patent No.: US 6,974,326 B2
(45) Date of Patent: Dec. 13, 2005

(54) METHOD OF AND AN APPARATUS FOR MEASURING A PERSON'S ABILITY TO PERFORM A MOTOR CONTROL TASK

(75) Inventor: Dilwyn Edwin Marple-Horvat, Worcester (GB)

(73) Assignee: The University of Bristol, Bristol (GB)

( * ) Notice: Subject to any disclaimer, the term of this patent is extended or adjusted under 35 U.S.C. 154(b) by 153 days.

(21) Appl. No.: 10/125,993

(22) Filed: Apr. 19, 2002

(65) Prior Publication Data

US 2003/0153846 A1    Aug. 14, 2003

(51) Int. Cl.[7] .......................... A63B 69/00; G09B 19/00
(52) U.S. Cl. ........................ 434/236; 434/69; 434/258; 600/300; 340/272
(58) Field of Search .............................. 434/29, 62, 64, 434/66, 69, 236, 238, 247, 258, 307 R, 308, 434/362, 365; 600/300, 558; 348/77, 114, 348/118; 180/272; 701/1; 382/118, 190, 382/209; 340/575, 576

(56) References Cited

U.S. PATENT DOCUMENTS

| | | | | |
|---|---|---|---|---|
| 4,768,088 A | * | 8/1988 | Ando | 348/77 |
| 5,366,376 A | * | 11/1994 | Copperman et al. | 434/69 |
| 5,570,698 A | * | 11/1996 | Liang et al. | 600/558 |
| 5,745,038 A | * | 4/1998 | Vance | 340/575 |
| 5,901,246 A | * | 5/1999 | Hoffberg et al. | 382/209 |
| 6,356,812 B1 | * | 3/2002 | Cragun | 701/1 |
| 6,575,902 B1 | * | 6/2003 | Burton | 600/300 |
| 6,644,976 B2 | * | 11/2003 | Kullok et al. | 434/236 |
| 6,717,518 B1 | * | 4/2004 | Pirim et al. | 340/576 |
| 2003/0136600 A1 | * | 7/2003 | Breed et al. | 180/272 |
| 2003/0169907 A1 | * | 9/2003 | Edwards et al. | 382/118 |
| 2004/0233061 A1 | * | 11/2004 | Johns | 340/575 |

* cited by examiner

Primary Examiner—Joe H. Cheng
(74) Attorney, Agent, or Firm—Reising, Ethington, Barnes, Kisselle, P.C.

(57) ABSTRACT

An apparatus is provided for assessing a persons ability to perform tasks requiring hand and eye co-ordination. A gaze tracker 6 images a person's eye in order to determine their direction of look. In the context of a vehicle system, a steering wheel direction sensor 12 is provided to determine the direction of the steering wheel. Data from the steering wheel sensor and the gaze tracker is compared by a data processor 14 which looks for correlations between the data sets and uses this correlation to determine whether the person 2 is fit to drive or not.

14 Claims, 5 Drawing Sheets

Figure 1:
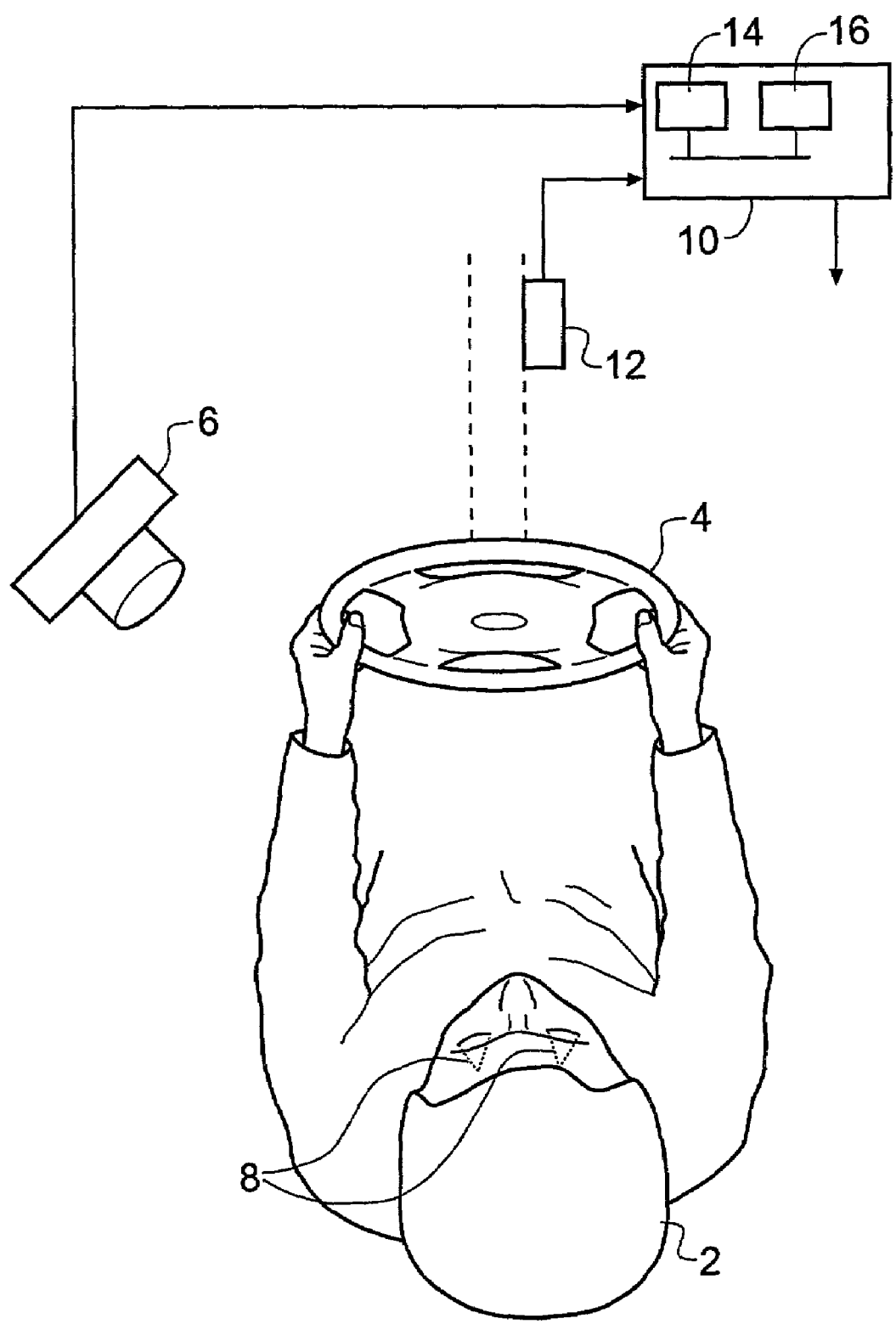

METHOD OF AND AN APPARATUS FOR MEASURING A PERSON'S ABILITY TO PERFORM A MOTOR CONTROL TASK

The present invention relates to a method of and apparatus for measuring a person's ability to perform a task which requires control of at least one of the person's limbs.

There are a number of tasks which are known to require hand and eye co-ordination. An everyday example of one of these tasks is driving a motor vehicle. A driver uses visual cues in order to accurately position the car with respect to the carriageway and to avoid other vehicles. It is, however, also well known that a person's ability to drive can become impaired. This impairment can be for several reasons, such as tiredness, use of alcohol, use of recreational pharmaceuticals, and use of prescribed pharmaceuticals where these have a side effect. The driver may also be generally inattentive or may be distracted by his environment—both external to the vehicle and internal to the vehicle.

According to a first aspect of the present invention, there is provided a method of measuring a person's ability to perform a task which requires control of at least one of the person's limbs, the method comprising:
 a) measuring a first motion which comprises the movement of at least one of the person's limbs, or the movement of a device operated by the person;
 b) measuring a second motion made by the person in order to acquire visual data in order to perform the first motion; and
 c) comparing the first and second motions to obtain a measure of performance.

The inventors have realised that it is possible to use a fairly well established correlation between direction of gaze and motion of a limb of a person and the performance of a spatially complex task in order to determine whether or not that person is competent to perform that task. In general, when a person seeks to manipulate an object, they often glance towards that object prior to manipulating it. This correlation has also been observed in people performing tasks such as driving. In general, as a driver approaches, for example, a left hand bend in the road their gaze will divert to the left just prior to reaching the bend. The strength of the correlation between the change in the direction of gaze of the driver and the action of turning the steering wheel in order to position the car has been found by the inventors in tests to represent a good statistical measure of the fitness of the driver to drive. However the present invention can be extended to other hand eye co-ordination tasks such as flying or operating complex machinery. Fitness to drive can relate to whether a driver is tired, drugged or drunk, or whether the driver is inattentive, for example, because they are distracted by an in-vehicle display (such as an entertainment system) or because they are using a mobile telephone.

It has to be recognised that performance between the individuals in a population may vary widely. It is thus advantageous to compare a measurement of the current performance of an individual with a historical measurement of their performance in order to determine whether their performance has been degraded, for example because of the use of alcohol. The historical performance may for example be from data derived several minutes or hours earlier, or in the case of a vehicle, the last time the vehicle was used.

Advantageously, a longer term measurement of the historical performance of a person performing a task may also be derived. This could be achieved by averaging data over several hours, or by parameterising the data such that it is more compact.

In the specific context of an automobile, it is possible that the vehicle will be driven by several different drivers. It may then be necessary to have the drivers identify themselves to the vehicle prior to starting. However, this need may be reduced or obviated if certain biometric data is made available to the vehicle for each driver, such as their weight and seat position. Thus the vehicle may be able to automatically identify each of its standard set of drivers and apply the appropriate data set for assessing that driver's performance.

Preferably measurements are made of a persons direction of gaze in order to acquire the second motion made by the person in order to acquire visual data. Commercial eye-tracking systems are available and need not be described herein.

Preferably a measure of inter-relation between the first and second motions is derived.

Advantageously the first and second motions are cross-correlated with each other in order to obtain a maximum value of the cross-correlation and time difference between the sets of data. Both the maximum value (peak value) of the cross-correlogram (ie the result of the cross-correlation analysis) and the time delay which corresponds to this peak value are measurements of the person's performance at performing tasks requiring hand and eye (or other limb) co-ordination.

Advantageously the data is divided into time frames, and results within one time frame are compared with the results of previous time frames. A time frame may span several minutes. It is advantageous to provide a comparison between recent historical data and more long term historical data. It could be envisaged that a driver who has, for example, driven to a public house (i.e. a bar), had a few drinks, and then returned to his vehicle will show a marked deterioration in performance between data acquired just prior to visiting the public house, and data acquired immediately after visiting the public house. Thus a comparison between present and recent historical data will yield a significant difference. However, it will also be appreciated that on a long drive, a driver may gradually become inattentive, for example as they begin to fall asleep. Thus the change will be relatively slow and in particular the change from one measurement set taken in a time frame to the next measurement set will be almost negligible. However, a comparison of most recent data with data taken several hours earlier should reveal a significant variation. It is therefore advantageous if the historical data comprises a weighted sum of recent data and older data. The older data may be derived from the driving performed over a period spanning several, for example 10 hours, proceding the current time. Only actual driving time is counted in this data set. Thus, if a driver parks their car at night, the clock is effectively stopped thereby preventing the data from being discarded.

It is possible that a driver's performance may vary slightly during the day and therefore some allowance may be made for the actual time of day that the data is captured.

If, as a result of the comparison between recent data and historical data, it is judged that the driver's performance has fallen below the historical indication of their performance by more than a predetermined threshold, a warning may be issued or an action ay be taken. The warning may be in the form of an audible or visual warning presented to the driver to suggest that they are no longer fit to continue using the car. However, it could be envisaged that the result of the comparison could also be used to inform the driver that the engine management system will disable motion of the car in several minutes time and that they have a limited period in which to park the car safely before it becomes immobilised. In an alternative arrangement, the engine management system may be responsive to this data in order to limit the maximum speed of the car to a low speed in order to minimise the risk to both the driver and third parties.

It is also possible that there is a correlation between a driver's performance and some activity within the vehicle. For vehicles having vehicle management systems or entertainment systems having a television like display (ie a display capable of displaying moving images or similar) then there may be adverse effects on the driver's performance if the driver becomes distracted by the display. The driver's performance may be correlated with the operation (or mode of operation) of such devices and the devices may be inhibited or switched to a different mode if the result of the correlation indicates that the driver is being distracted.

This concept can be extended further by inhibiting the use of entertainment systems or communication systems if a driver's historical or present data indicates that the particular driver is distracted to a level deemed to be significant by such systems. In this context "significant" may denote a relative change in driver performance and/or performance parameters falling below an absolute threshold.

Preferably, in the context of an automobile based system the first motion is derived from measurements of the steering wheel position.

According to a second aspect of the present invention, there is provided an apparatus for measuring a person's ability to perform a task requiring control of limb position, the apparatus comprising:
 a) a first input device responsive to motion of at least one limb;
 b) an eye-tracker for determining the person's direction of gaze; and
 c) a data processor for comparing an output of the first input device with an output of the eye-tracker, and for making the result of the comparison available.

According to third aspect of the present invention, there is provided a vehicle incorporating an apparatus constituting an embodiment of the second aspect of the present invention.

Preferably the vehicle is an automobile.

According to a fourth aspect of the present invention, there is provided a computer program for causing a data processor to perform the method according to the first aspect of the present invention.

Figure 3:
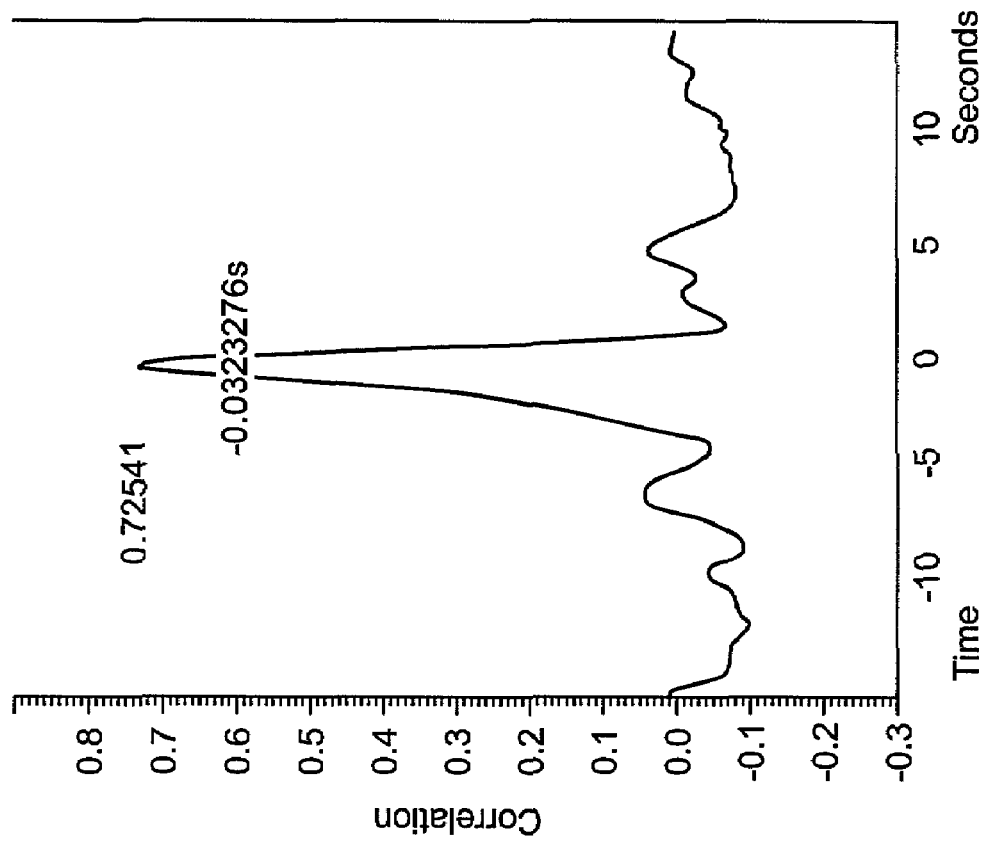
Figure 2:
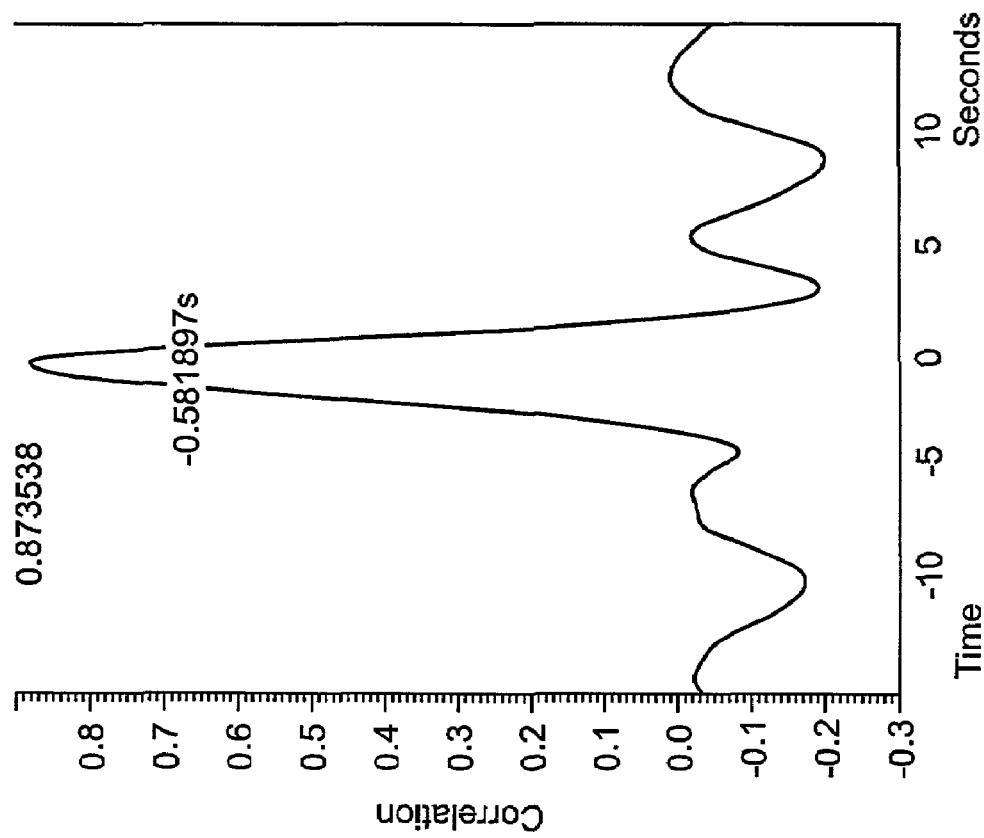
Figure 4A:
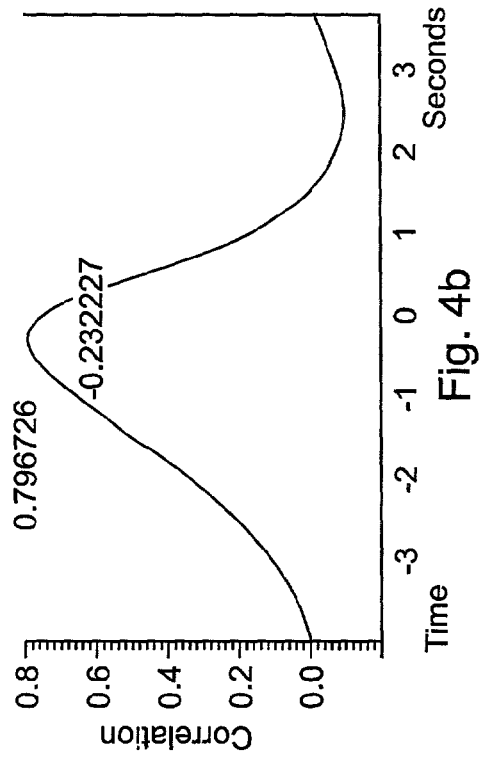
Figure 4B:
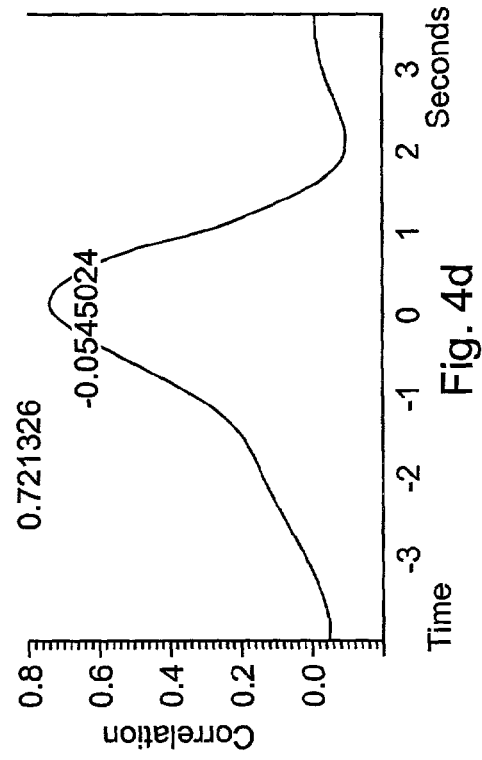
Figure 4C:
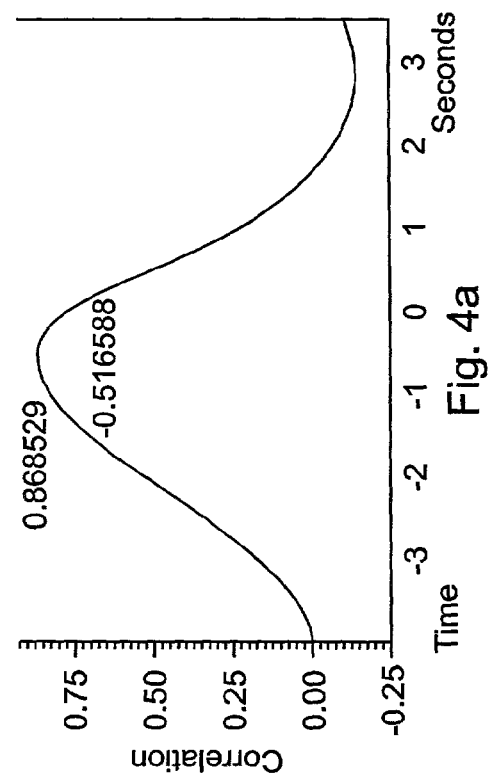
Figure 4D:
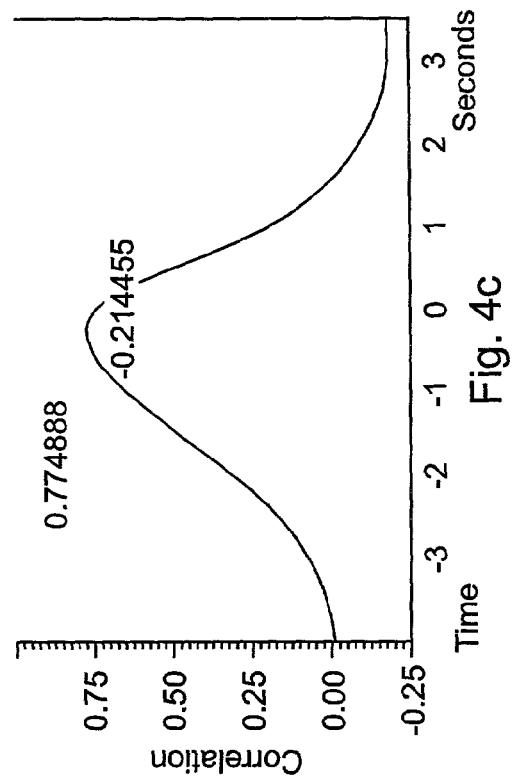
Figure 5:
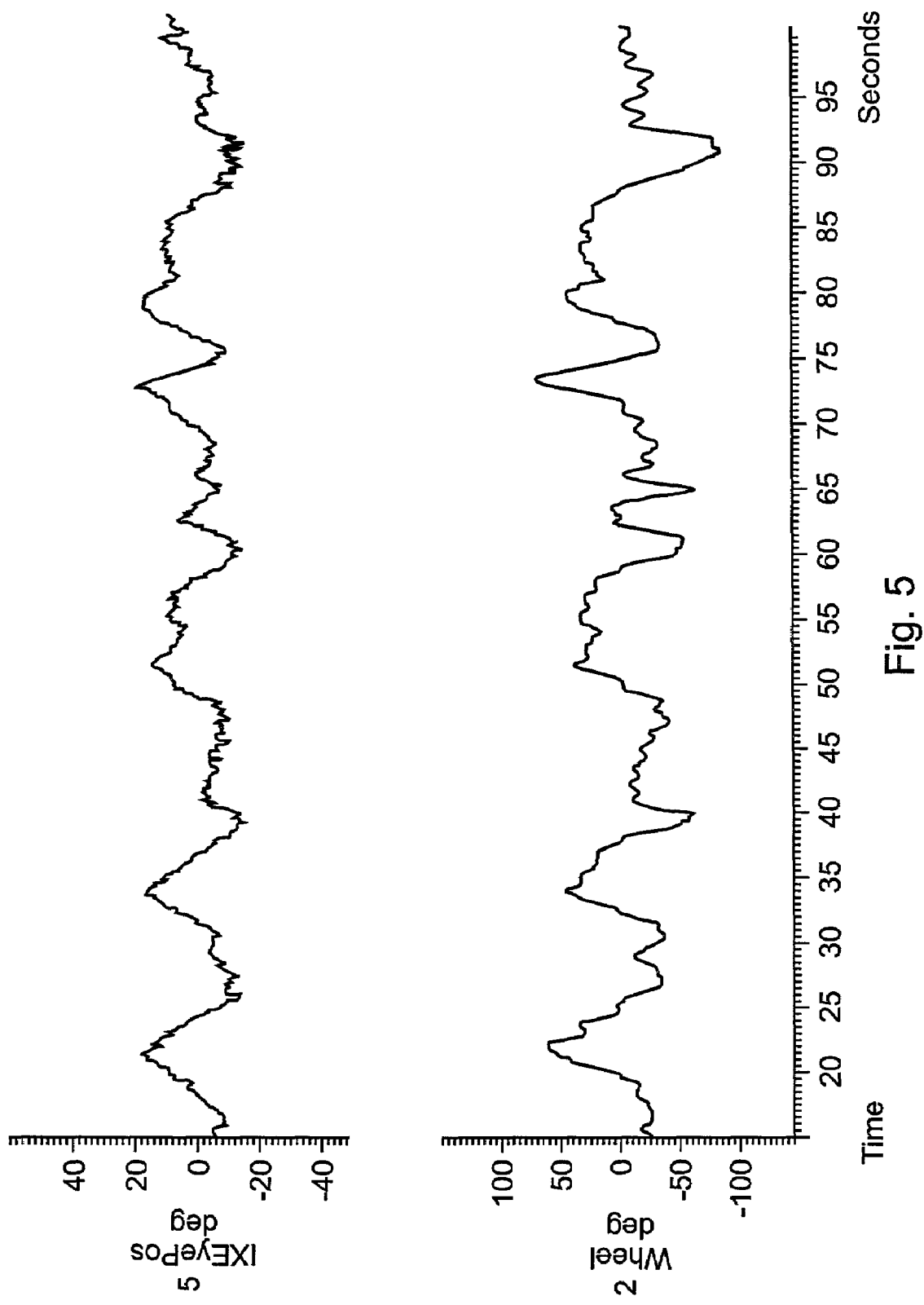
Figure 6:
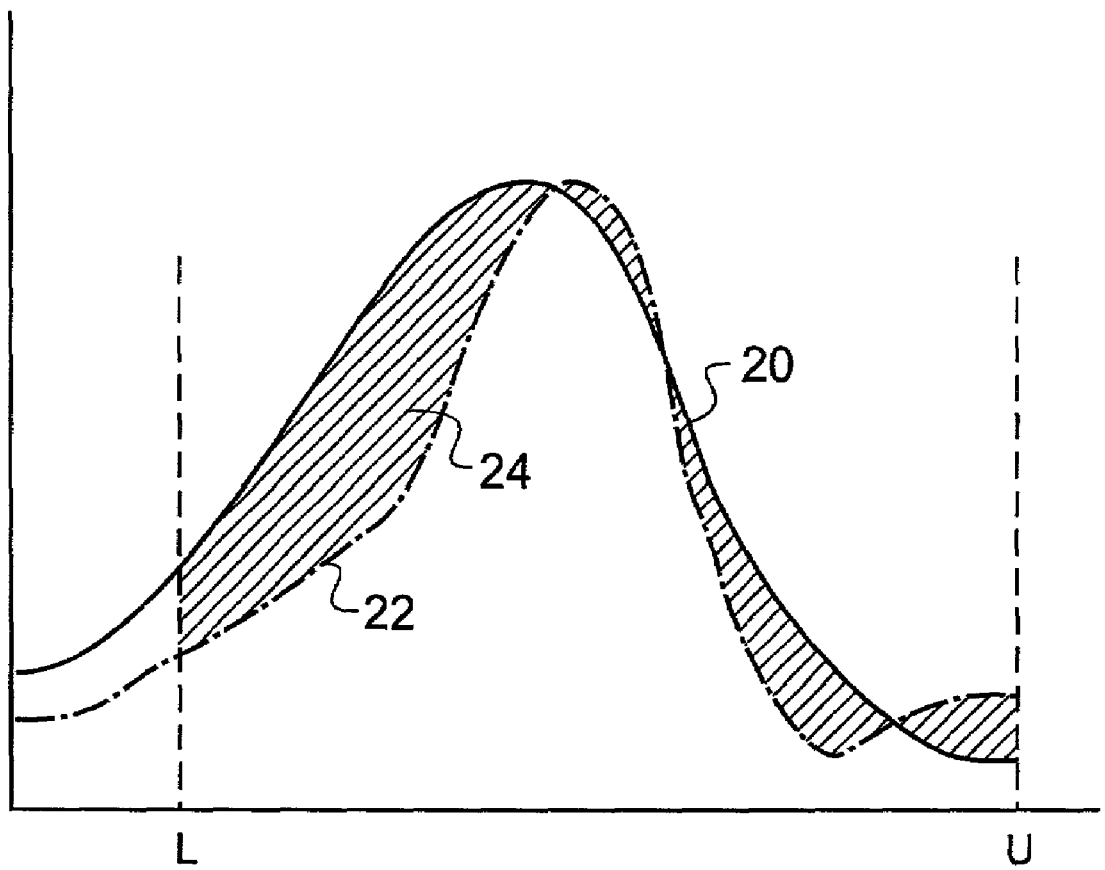

The present invention will further be described, by way of example, with reference to the accompanying figures, in which:

FIG. 1 schematically illustrates an in-car apparatus constituting an embodiment of the present invention for comparing a driver's direction of gaze with their actions:

FIG. 2 schematically illustrates a cross-correlogram between eye movement and steering wheel position for a driver who is not under the influence of alcohol;

FIG. 3 schematically illustrates a cross-correlogram for the same driver when under the influence of alcohol;

FIGS. 4a to 4d schematically illustrate the cross-correlogram of a driver as they start from sober (FIG. 4a) and become increasingly intoxicated (FIG. 4d);

FIG. 5 illustrates the correlation between direction of gaze and steering wheel position for a subject in a driving simulator; and FIG. 6 illustrates the use of a non-overlapping integral as a measure of driver performance.

It is known that whilst performing a complex task such as driving, a driver is constantly adjusting their gaze in order to chart their progress along the carriageway, and also to follow the motion of oncoming vehicles. However, it is also known (see for example Nature, Vol. 369, 30th Jun. 1994, page 707 and 742, M. F. Land and D. N. Lee) that drivers show a strong tendency to fixate along a tangent from the car to the inside edge of the road when turning a corner. In fact, the direction of gaze is highly correlated with the direction of steering. This correlation is not perfect as the driver's gaze can be distracted by other objects moving along the roadside.

The present inventors have realised that control of eye motion is surprisingly complex and becomes rapidly adversely affected by drink and drugs and even tiredness. By investigating the correlation further between direction of gaze and steering angle of the vehicle, the inventors have realised that it is in fact a useful predictor of a person's competency to drive. FIG. 5 is a graph showing two traces. The upper trace represents a person's direction of gaze, and the lower trace represents the direction of a steering wheel when presented with a task of keeping a car on a simulated road. Although the traces contain some noise, it is fairly clear that the peaks in the graph of the direction of gaze are followed fairly rapidly by peaks in the graph of steering wheel position, and similarly troughs in the direction of gaze graph are rapidly followed by troughs in the graph of steering wheel position.

FIG. 1 schematically illustrates an automobile including an apparatus for assessing drive competency constituting an embodiment of the present invention.

As shown in FIG. 1, a driver 2 is positioned adjacent a steering wheel 4 such that he can control the direction of a vehicle (not shown) in which he is sitting. A direction of gaze monitor 6 repeatedly forms images of the driver's eyes 8 and uses this to calculate the direction in which the driver is looking. An output of the direction of gaze monitor 6 is provided to a first input of a data processor 10. A steering wheel position sensor 12 is provided to monitor the angular position of the steering wheel 4. An output of the steering wheel position monitor 12 is provide to a second input of the data processor 10. The data processor includes a processing unit 14 in association with memory 16. The memory 16 acts to hold the instructions necessary to cause the data processor 14 to receive and compare the outputs of the direction of gaze monitor 6 and the steering wheel position sensor 12. The data processor 10 compares the evolution in time of the signals representing the driver's direction of gaze and the motion of the steering wheel and checks to see whether these are correlated with respect to one another to a sufficient level of correlation.

Referring to FIG. 5 again, it can be seen that the upper trace and the lower trace are very similar with one being a time shifted version of the other. By performing cross-correlation, the traces are effectively multiplied with respect to each other at various different relative time shifts. The result of this multiplication yields a single correlation value for each different time shift between the two graphs. This process is repeated many times for different time shifts and results in a cross-correlation graph (also known as a cross-correlogram). A cross-correlation graph is shown in FIG. 2 for a test subject who was sober. It could be seen that there is a clear peak in the cross-correlation graph, with the peak having a value of 0.873538. (It is known to the person skilled in the art that the correlation coefficient is constrained to lie within the range +1 to −1). It can also be seen that the peak occurs at a time shift of approximately 0.58 seconds.

This shows for the test subject when sober, their direction of gaze leads the direction of turn of the steering wheel by approximately 0.6 second.

FIG. 3 shows the cross-correlation graph for the same subject a consuming a degree of alcohol. It can be seen that the maximum value of the correlation peak has reduced to approximately 0.73. It can also be seen that the motion of the eyes now barely leads the motion of the steering wheels with the time difference having reduced to 0.03 seconds. Thus the reduction in height of the cross-correlation peak, and the reduction of the lead time between the motion of the eyes and the motion of the steering wheel are both indicators of reduced driver performance.

FIGS. 4a to 4d are cross-correlation graphs for a subject as they start from sober at graph 4a and drink increasing amounts of alcohol, finally ending up at graph 4d. It will be seen that as the amount of alcohol increases, the cross-correlation peak diminishes from a value of 0.87 to 0.80, then to 0.77 and finally to 0.72. In association with this, the time by which the motion of the eyes leads the motion of the steering wheel decreases from 0.52 seconds to 0.23, 0.21 and finally 0.05 seconds. It can be seen that the reduction in the height of the correlation peak is substantial and significant, changing by approximately 20%, the reduction in time by which the eyes lead the motion of the steering wheel is also significant, changing by a factor of 10.

The subject whose performance is shown in FIGS. 4a to 4d was a young female driver. For FIG. 4b she had drunk 40 ml of 45% vodka, which is equivalent to between one and two vodka and oranges in a standard public house. For FIG. 4c she had drunk a total of 70 ml, and for FIG. 4d this was increased to a total of 100 ml—which is equivalent to 4 single vodkas and orange.

In order to assess the performance of a driver, the data processor 10 must first learn the average performance of a driver over a period of time. It is expected that a driver's eye lead time and cross-correlation peak height will be individual to that driver. However, it is envisaged that it may be possible to set up global values indicating acceptable standards of performance for a vast majority of the driving population. This global standard or history of a drivers own performance may then be used to judge the driver's current performance. In particular, a driver may be issued a warning once the data processor determines that the driver's driving parameters have dropped below the predetermined proportion of the normal parameters for that driver. Thus, if a driver's normal correlation peak has a value of 0.85, a warning may be issued to the driver once they fall below a predetermined proportion, for example 90%, of their normal performance. Thus a warning might be issued to a driver once the height of the correlation peak drops below 0.76 for the most recent time period in which the driver performance has been monitored.

Additionally and/or alternatively, the time lead between a driver's eye movement and the motion of the steering wheel may be monitored. A warning may be issued when the lead is reduced by a predetermined portion, for example 50%. These two measurements can be combined and a weighted sum of the driver performance may be formed as a performance metric.

A further method for assessing the change in a driver's response over time is to compare a current cross-correlogram with a historical cross correlogram by calculating a non-overlapping integral. This is schematically illustrated in FIG. 6 where the area on the graph between the curves of the two cross-correlograms and bounded by upper and lower limits is shown hatched. In FIG. 6, the upper curve represented by a solid line 20 is a tracing of the curve shown in FIG. 4A and a lower curve represented by a chain dot line 22 is a tracing of the curve shown in FIG. 4D. The hatch region 24 therefore represents a measurement of a difference between the two curves. The non-overlapping integral is bounded by upper and lower limits U and L, respectively, which in this example are set at +3 and −3 seconds. This form of comparison is particularly suited to implementation within digital computers since the process of digitisation results in each correlogram being represented as a simple list of numbers spanning the period L to U with consecutive entries in the list separated by the sampling interval. Calculation of the non-overlapping integral is by simple subtraction of values in the historical list from equivalent values in the current list to produce a difference, followed by the summing of the absolute value of all the numbers in the difference list. Thus calculation of the non-overlapping integral is computationally efficient. Large areas (ie a large number resulting from the above calculation) identified by this process indicate that driver performance has changed significantly and a warning may be issued, for example once the area exceeds the threshold value. The area identified by the non-overlapping integral may be used to give a quantitative or qualitative measure of driver alertness or intoxication.

It should be noted that, for mathematical convenience, the area of the non-overlapping integral can be defined as that area limited by the upper and lower boundaries, and below one of the cross correlograms, but not below both of them.

The driver's performance may be repeatedly measured in a series of time periods and the results of these measurements may be parameterised, for example lead time and correlation peak height. The evolution with time of these parameters may be analysed by the data processor in order to determine an accurate range of driver performance which may account for time of day and also the duration that a driver has been driving. These parameters can then be used to provide a reliable indication of the driver's normal range of eye lead time and correlation coefficients such that it thus becomes possible to warn a driver if their performance is beginning to flag for example because of tiredness or illness.

The driver data may also be monitored to look for a frequency distribution of eye movement and wheel movement, that is how much time the eyes are looking in any particular direction and the time that the wheel is turned in that particular direction. From this data a difference distribution can be formed and a variation in the difference distribution may also be used to initiate a warning to a driver.

Advantageously the data processor keeps an historical log of data. Thus the data processor may be used by the authorities to assess the driver's performance in the event that the driver has an accident. Thus this data may be used to infer the fitness of a driver to drive at the time of the accident.

Advantageously the data processor would also be arranged to issue a warning if the eye tracking signal was lost for any significant period of time. This might be because, for example, the driver's eyes have begun to close through tiredness.

The apparatus may also be used to detect driver distraction—which is expected to manifest itself as a reduction in lead time and/or a variation in frequency distribution of eye movement. Such distraction may result from operation of in-vehicle information or entertainment systems.

It is thus possible to provide a method of and apparatus for assessing the ability of a person to perform tasks requiring hand and eye co-ordination and in particular to provide an apparatus for assessing whether a person is fit to drive.

What is claimed is:

1. A method of determining whether a person's ability to drive a motor vehicle has become impaired, the method comprising the steps of:
   a) measuring eye movement made by a person in order to acquire visual data for driving a vehicle;
   b) measuring a control motion made by the person in order to control the direction of the vehicle;
   c) comparing the person's eye movement with the control motion made by the person in order to obtain a measure of the person's performance; and
   d) comparing the measurement of performance with a threshold and to output the result of the comparison.

2. A method as claimed in claim 1, wherein the measure of performance is compared with a historical measure of performance and one item selected from the group consisting of issuing a warning and taking an action, is performed if the difference exceeds a predetermined threshold.

3. A method as claimed in claim 1, wherein the eye motion as a function of time and the control motion as a function of time are cross-correlated.

4. A method as claimed in claim 3, wherein the cross-correlation is analysed to determine at least one of a correlation peak value and a time displacement.

5. A method as claimed in claim 4, wherein the results from a recent cross-correlation are compared with a historical measure, and one item selected from the group consisting of issuing a warning and taking an action, is performed if the correlation peak value is less than the historical measure by a threshold amount.

6. A method as claimed in claim 5, wherein the warning is issued when a value of the recent cross-correlation peak is less than the product of an acceptance coefficient and the historical value of the cross-correlation peak.

7. A method as claimed in claim 5, wherein the results of a recent cross-correlation are compared with a historical measure by forming a non-overlapping integral and a warning is issued depending upon the size of the integral.

8. A method as claimed in claim 1, wherein the control motion is determined by measuring motion of a steering wheel.

9. An apparatus for determining whether a person's ability to drive a motor vehicle has become impaired, the apparatus comprising:
   a) an eye tracker for measuring the person's eye movements to acquire visual data for driving the vehicle;
   b) a motion sensing device for measuring a control motion made by the person in order to control the direction of the vehicle; and
   c) a data processor for comparing an output of the eye tracker with an output of the motion sensing device to derive a measure of the person's performance and to compare the measure of performance with a threshold and to output the result of the comparison.

10. An apparatus as claimed in claim 9, wherein the data processor is arranged to cross-correlate the output of the motion sensing device with an output of the eye-tracker.

11. An apparatus as claimed in claim 9, wherein the result of the comparison is compared with historical data, and one of a warning issued and a predetermined action taken if the difference exceeds a predetermined threshold.

12. An apparatus as claimed in claim 9, wherein the motion sensing device is responsive to motion of a steering wheel.

13. A motor vehicle, including an apparatus for determining whether a person's ability to drive the motor vehicle has become impaired, the apparatus comprising:
   a) an eye tracker configured to measure eye movements made by a driver to acquire visual data for driving the motor vehicle;
   b) a motion sensing device configured to measure a control motion made by the driver to control the direction of the motor vehicle; and
   c) a data processor programmed to compare an output of the eye tracker with an output of the motion sensing device to derive a measure of the driver's performance and to compare the measure of performance with a threshold and to output the result of the comparison.

14. A computer program storage device readable by a machine, tangibly embodying a program of instructions executable by the machine to perform method steps for determining whether a person's ability to drive a motor vehicle has become impaired, the method comprising the steps of:
   a) measuring eye movement made by a driver to acquire visual data for driving a vehicle;
   b) measuring a control motion made by the driver to control the direction of the vehicle;
   c) obtaining a measure of the driver's performance by comparing the eye movement made by the driver with the control motion made by the driver; and
   d) comparing the measurement of the driver's performance with a threshold and outputting a result of the comparison.

* * * * *